United States Patent
Kweon et al.

(10) Patent No.: US 10,786,335 B2
(45) Date of Patent: *Sep. 29, 2020

(54) DENTAL BARRIER MEMBRANE USING SILK MATRIX AND METHOD OF MANUFACTURING THE SAME

(71) Applicant: REPUBLIC OF KOREA (MANAGEMENT:RURAL DEVELOPMENT ADMINISTRATION), Jeonju-si, Jeollabuk-do (KR)

(72) Inventors: Hae-Yong Kweon, Suwon-si (KR); You-Young Jo, Jeollabuk-do (KR); Kwang-Gill Lee, Suwon-si (KR); Kee-Young Kim, Jeollabuk-do (KR)

(73) Assignee: Republic of Korea (Management: Rural Development Administration), Jeonju-si, Jeollabuk-do (KR)

( * ) Notice: Subject to any disclaimer, the term of this patent is extended or adjusted under 35 U.S.C. 154(b) by 98 days.

This patent is subject to a terminal disclaimer.

(21) Appl. No.: 15/577,803

(22) PCT Filed: Jun. 7, 2016

(86) PCT No.: PCT/KR2016/005963
§ 371 (c)(1),
(2) Date: Nov. 29, 2017

(87) PCT Pub. No.: WO2017/069366
PCT Pub. Date: Apr. 27, 2017

(65) Prior Publication Data
US 2018/0168778 A1  Jun. 21, 2018

(30) Foreign Application Priority Data
Oct. 21, 2015 (KR) .................. 10-2015-0146676

(51) Int. Cl.
A61C 8/02 (2006.01)
A61C 8/00 (2006.01)
(Continued)

(52) U.S. Cl.
CPC .......... A61C 8/0016 (2013.01); A61C 8/0006 (2013.01); A61C 8/0031 (2013.01);
(Continued)

(58) Field of Classification Search
CPC ... A61C 8/0016; A61C 8/0006; A61C 8/0031; G01N 2333/43578; B29C 43/003;
(Continued)

(56) References Cited

U.S. PATENT DOCUMENTS

| 6,689,374 B2 | 2/2004 | Chu et al. |
| 2006/0095137 A1 | 5/2006 | Chung et al. |
| 2008/0292667 A1 | 11/2008 | Chung et al. |

FOREIGN PATENT DOCUMENTS

| JP | H06-166850 A | 6/1994 |
| JP | 2006-070404 A | 3/2006 |

(Continued)

OTHER PUBLICATIONS

Ha, Y, et al "Comparison of the Physical Properties and In Vivo Bioactivities of Silkworm-Cocoon-Derived Silk Membrane, Collagen Membrane, and Polytetrafluoroethylene Membrane for Guided Bone Regeneration", Macromolecular Research, vol. 22, No. 9, pp. 1018-1023 (2014) (Year: 2014).*

(Continued)

Primary Examiner — Brian A Dukert
Assistant Examiner — Rebecca Lynee Zimmerman
(74) Attorney, Agent, or Firm — Rabin & Berdo, P.C.

(57) ABSTRACT

Disclosed are a dental barrier membrane for guided bone regeneration using a silk matrix and a method of manufacturing the same, wherein the dental barrier membrane is (Continued)

configured such that a silk matrix having a cross-section with a first thickness, produced from silkworms, is subjected to planar division into two or more silk matrix pieces having a predetermined shape with the first thickness. This dental barrier membrane is biocompatible, has superior tensile strength and porosity, and promotes the formation of new bone in bone defects, unlike existing dental barrier membranes.

18 Claims, 8 Drawing Sheets

(51) Int. Cl.
  *A61L 27/36* (2006.01)
  *D01B 7/02* (2006.01)
  *D01B 7/06* (2006.01)
(52) U.S. Cl.
  CPC ............ *A61L 27/3604* (2013.01); *D01B 7/02* (2013.01); *D01B 7/06* (2013.01)
(58) Field of Classification Search
  CPC .......... C07K 14/43586; C07K 2317/76; A61L 27/3604; D01B 7/02; D01B 7/06
  See application file for complete search history.

(56) References Cited

FOREIGN PATENT DOCUMENTS

| KR | 10-2006-0038096 A | 5/2006 | |
|---|---|---|---|
| KR | 10-2014-0003942 A | 1/2014 | |
| KR | 10-1403473 B1 | 6/2014 | |
| KR | 10-1602791 B1 | 3/2016 | |
| KR | 10-1602797 B1 | 3/2016 | |
| WO | WO-2011156586 A2 * | 12/2011 | ......... A61L 27/3604 |

OTHER PUBLICATIONS

Zhao, H. et al "Mechanical Properties of Silkworm Cocoons" Polymer, 46; 9192-9201 (2005) (Year: 2005).*

Garay, L.B., et al. (2014) New Technique to Produce Large Amount of Flat Silk by Biospinning. Agricultural Sciences, 5, 1483-1490. (Year: 2014).*

You-Young Jo et al., "Preparation and characterization of medical silk sponge", Journal of Sericultural and Entomological Science, vol. 51, pp. 68-69, 2013; English abstract.

* cited by examiner

<Inventive dental barrier membrane>

4 weeks after surgery　　　8 weeks after surgery

<Collagen barrier membrane>

4 weeks after surgery　　　8 weeks after surgery

<PTFE barrier membrane>

4 weeks after surgery　　　8 weeks after surgery

DENTAL BARRIER MEMBRANE USING SILK MATRIX AND METHOD OF MANUFACTURING THE SAME

TECHNICAL FIELD

The present invention relates to a dental barrier membrane for guided bone regeneration using a silk matrix and a method of manufacturing the same and, more particularly, to a dental barrier membrane using a silk matrix and a method of manufacturing the same, wherein the dental barrier membrane is biocompatible, has superior tensile strength, and promotes the formation of new bone in bone defects, unlike existing dental barrier membranes.

BACKGROUND ART

A dental barrier membrane for guided bone regeneration is used to induce bone regeneration in bone defects during a dental implant operation, as necessary. It functions to hold the space necessary for bone regeneration until the bone is regenerated by mechanically blocking epithelial or connective tissue cells from moving to the bone defects.

An initially useful membrane has been formed using a non-degradable material, such as polytetrafluoroethylene, cellulose acetate, silicone rubber or polyurethane. However, the non-degradable material used for such a membrane is a synthetic polymer material and thus has low biocompatibility, undesirably causing inflammation or tissue necrosis.

With the goal of solving such problems, there is ongoing thorough research into biodegradable membranes having high biocompatibility using a natural material such as collagen. Biodegradable membranes are not very different in terms of bone regenerative capacity from membranes made of non-degradable material. However, when biodegradable membranes are applied to clinical cases, they do not exhibit sufficient tensile strength, thus making it impossible to retain the morphology of the membrane and to ensure the space necessary for growing the tissue, undesirably incurring secondary inflammation of the material.

Therefore, dental barrier membranes having biocompatibility using a natural material and sufficient tensile strength to retain the morphology of the membrane are still under study.

The related techniques include Korean Patent Application Publication No. 10-2014-0003942 (Laid-open Date: Jan. 10, 2014, Title: Dental barrier membrane having good growth of soft tissue or bone tissues) and Korean Patent No. 10-1403473 (Registration Date: Jun. 11, 2014, Title: Dental membrane).

DISCLOSURE

Technical Problem

Accordingly, an object of the present invention is to provide a dental barrier membrane using a silk matrix and a method of manufacturing the same, wherein the dental barrier membrane is made of a natural material, and thus, is biocompatible, has high tensile strength and porosity, and promotes the formation of new bone in bone defects, unlike existing dental barrier membranes.

Another object of the present invention is to provide a dental barrier membrane using a silk matrix and a method of manufacturing the same, wherein the manufacturing process is simple, and thus the manufacturing cost may be reduced compared to when manufacturing typical dental barrier membranes.

The technical problem according to the present invention is not limited to the above objects, and other objects that are not described herein will be obviously understood by those having ordinary skill in the art from the following description.

Technical Solution

In order to accomplish the above objects, the present invention provides a dental barrier membrane using a silk matrix, which is configured such that a silk matrix having a cross-section with a first thickness, produced from silkworms, is subjected to planar division into two or more silk matrix pieces having a predetermined shape with the first thickness.

In addition, the present invention provides a dental barrier membrane using a silk matrix, which is configured such that a silk matrix having a cross-section with a first thickness, produced from silkworms, is subjected to thickness division into two or more silk matrix portions having a second thickness, which is less than the first thickness.

In addition, the present invention provides a dental barrier membrane using a silk matrix, which is configured such that a silk matrix having a cross-section with a first thickness, produced from silkworms, is subjected to planar division into two or more silk matrix pieces having a predetermined shape with the first thickness, and each of the silk matrix pieces having the first thickness is subjected to thickness division into silk matrix pieces having a second thickness, which is less than the first thickness.

Advantageous Effects

According to the present invention, the method of manufacturing a dental barrier membrane using a silk matrix includes a simple manufacturing process, thus reducing the manufacturing cost compared to when producing typical dental barrier membranes.

Also, according to the present invention, the dental barrier membrane using a silk matrix can exhibit superior biocompatibility and high tensile strength and porosity, and can promote the formation of new bone in bone defects, unlike typical dental barrier membranes.

BEST MODE

Unless otherwise stated, the meanings of the terms, descriptions, etc., disclosed in the present specification may be those that are typically used in the art to which the present invention belongs. Hereinafter, a detailed description will be given of the present invention.

A dental barrier membrane refers to an assistant membrane for use in repairing a bone defect that is created in bone tissue due to various dental diseases. The dental barrier membrane has to significantly improve the formation of bone in the bone defect and the bone defect around the implant, and to possess biocompatibility, so as to be safe when used in vivo, as well as properties suitable for a suture process.

Furthermore, a dental barrier membrane for guided bone regeneration should be made of a material that entails no concern about the infection of surgical wounds, does not cause tissue degeneration, generates less discomfort in periodontal tissue, closely contacts periodontal tissue, and exhibits superior cell growth capacity.

However, a conventional dental barrier membrane is problematic because acids such as lactic acid, glycolic acid, etc. are produced upon hydrolysis in vivo, thus lowering the pH, undesirably causing an inflammatory reaction and tissue toxicity. When the dental barrier membrane is pretreated using physical crosslinking or the like to impart the aforementioned properties, it may incur toxicity in vivo upon long-term application, or may remain as a foreign material in vivo.

Therefore, in the present invention, the dental barrier membrane for guided bone regeneration using a silk matrix is manufactured, the manufacture of which is relatively simple, thus reducing the manufacturing cost thereof compared to when producing typical dental barrier membranes. Furthermore, such a dental barrier membrane may promote the formation of new bone in bone defects, is biocompatible, and has superior tensile strength and high porosity. Below is a detailed description thereof, made with reference to various examples.

Figure 3:
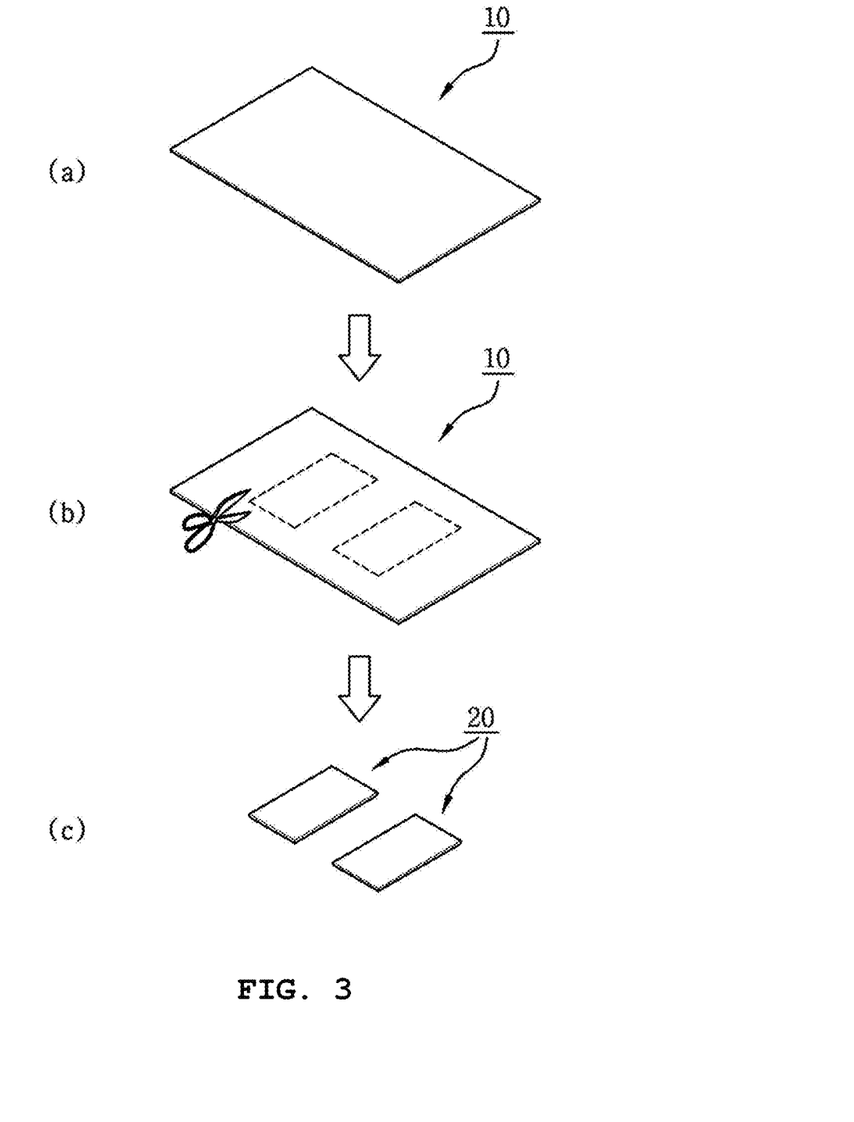
FIG. 3 illustrates the process of manufacturing the dental barrier membrane of Example 1 according to the present invention.

As illustrated in FIG. 3, the method of manufacturing a dental barrier membrane using a silk matrix of Example 1 according to the present invention is described below.

1. First Step: Preparation of Silk Matrix Pieces Having First Thickness

A silk matrix having a cross-section with a first thickness, produced from silkworms, is subjected to planar division into two or more pieces having an appropriate shape, thus obtaining silk matrix pieces having the first thickness.

When silkworms become mature silkworms to protect themselves, they begin to transform into pupae by spinning cocoons. When a silkworm transforms into a pupa, it spins a cocoon to make a pupal casing having a round and elongated shape. The casing is oval-shaped, and shows various colors depending on the kind of silkworm, and both ends thereof are slightly pointed and are thick. However, in the course of building cocoons by the silkworms, when a sheet on which the silkworms are placed is moved so as to disturb the formation of normal cocoons by the silkworms, silkworms do not make cocoons. The silkworms are artificially induced to spin cocoons on the sheet by moving the sheet on which the silkworms are placed, whereby the cocoons are spun in the form of a planar sheet, yielding a silk matrix.

Figure 1:
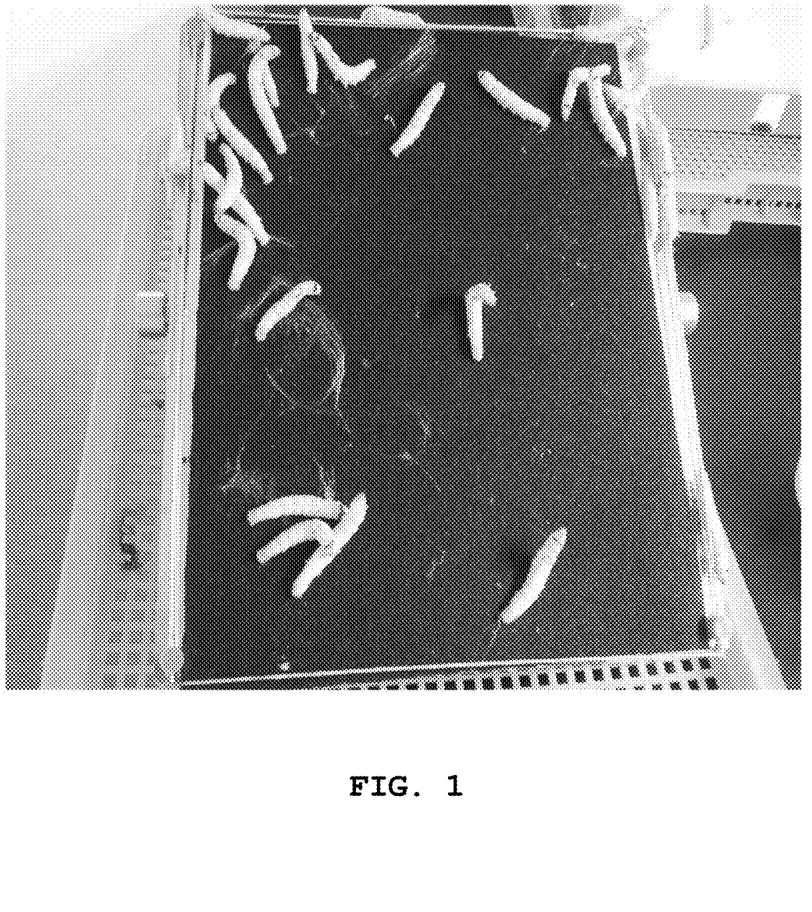
FIG. 1 illustrates the production of a silk matrix for use in a dental barrier membrane for guided bone regeneration according to the present invention, from silkworms.

Based on the above features, as illustrated in FIG. 1 according to an embodiment of the present invention, silkworms are placed on a sheet, and the sheet is tilted at a slope (15 to 30') to an extent that the silkworms are prevented from falling off the sheet, so that the silkworms are forced to move on the sheet and induced to spin cocoons, thus preparing a silk matrix (FIGS. 2A and 2B), having a cross-section with a first thickness, of interest in the present invention, which is then subjected to planar division into two or more pieces having an appropriate shape so as to be suitable for desired applications, yielding silk matrix pieces 20 having the first thickness, as illustrated in FIG. 3. Briefly, the silk matrix having a cross-section with a first thickness is subjected to planar division using a cutter such as a blade or scissors, thus forming the silk matrix pieces 20 having the first thickness and an appropriate shape.

Figure 2:
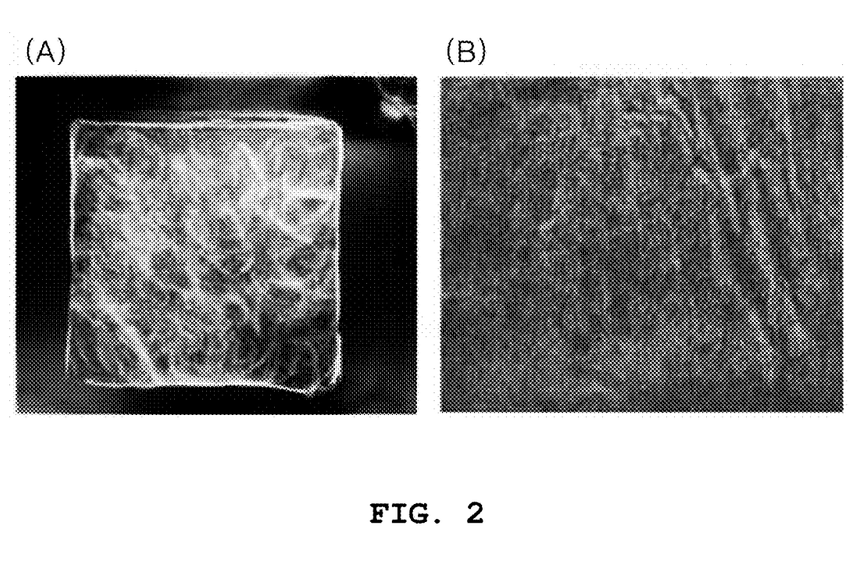
FIGS. 2A and 2B illustrate the results of visual observation of the morphology of the silk matrix at different thicknesses of 0.01 mm and 0.7 mm, respectively, used for a dental barrier membrane according to the present invention.

As illustrated in FIG. 2A, the silk matrix pieces 20 having the first thickness and the appropriate shape, obtained by subjecting the silk matrix 10 having the first thickness to planar division, may be used unchanged because the silk matrix 10 having the first thickness is produced to a thickness suitable for use as a dental barrier membrane. Further, packing or sterile treatment and chemical treatment may be additionally performed, as necessary.

In the case where the sheet on which silkworms are placed is moved to form a silk matrix, the movement thereof may be carried out variously. The sheet may be moved in a manner of being rotated, repeatedly tilted upward and downward and/or leftward and rightward, or vibrated. Alternatively, the sheet may be moved through a combination of rotation and repeated tilting upward and downward and/or leftward and rightward. The number or rate of movement or tilting processes may be appropriately set in order to ensure that the silk matrix has the desired shape.

The shape of the sheet on which silkworms are placed is not limited. A circular shape or a rectangular shape may be applied. Alternatively, any shape may be applied so long as silkworms do not spin cocoons normally in response to the movement of the sheet.

Figure 4:
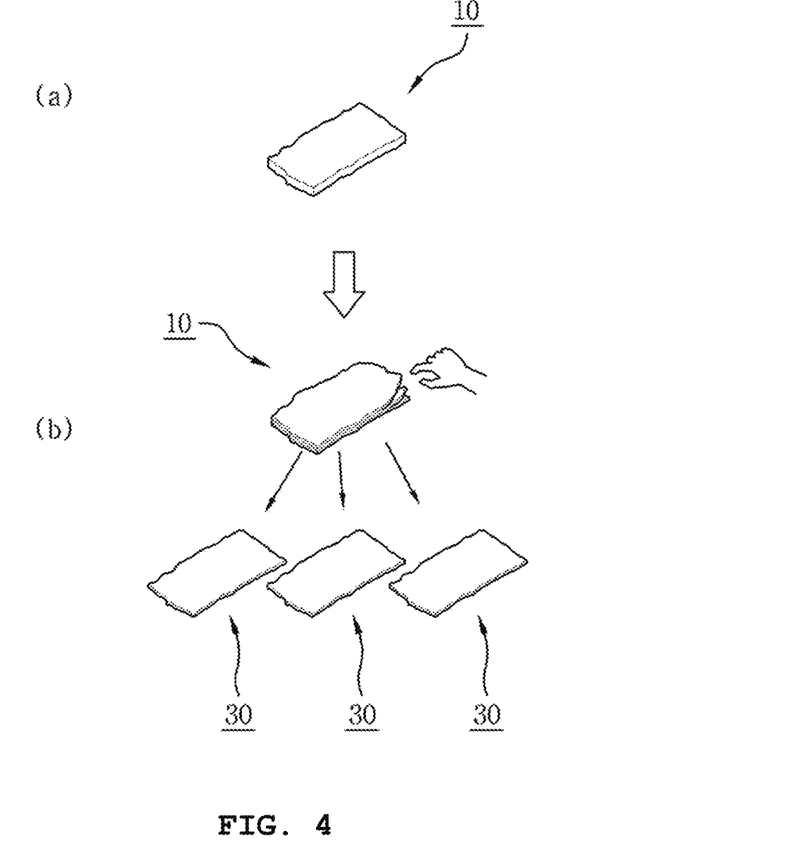
FIG. 4 illustrates the process of manufacturing the dental barrier membrane of Example 2 according to the present invention.

In another modification, the method of manufacturing a dental barrier membrane using a silk matrix of Example 2 according to the present invention, as illustrated in FIG. 4, is specified below.

1. First Step: Preparation of Silk Matrix Portions Having Second Thickness

A silk matrix having a cross-section with a first thickness, produced from silkworms, is subjected to thickness division into two or more portions having a second thickness, which is less than the first thickness.

The silk matrix 10 having the first thickness is produced from silkworms in such a manner that silkworms spin cocoons while being forced to move on the sheet, as in the description of FIG. 3. The silk matrix 10 having the first thickness may be configured as illustrated in FIG. 2B such that yarns resulting from spinning cocoons from the silkworms are stacked in a height direction to thus form various thicknesses (multiple layers).

The first thickness of the silk matrix 10 may vary depending on the number of silkworms used to prepare the silk matrix and the period of time that the silkworms require to spin cocoons.

As shown in FIG. 4, when the silk matrix 10 having the first thickness is thick, it may be subjected to thickness division into two or more portions having a thickness suitable for use in a dental barrier membrane, thus forming silk matrix portions 30 having a second thickness. The second thickness is less than the first thickness owing to such thickness division.

The silk matrix portions 30 having the second thickness may be used unchanged as the dental barrier membrane. Alternatively, portions of the silk matrix portions 30 having the second thickness may be utilized by adjusting the size thereof so as to be suitable for some end use. Further, packing or sterile treatment and chemical treatment may be additionally performed, as necessary.

Figure 5:
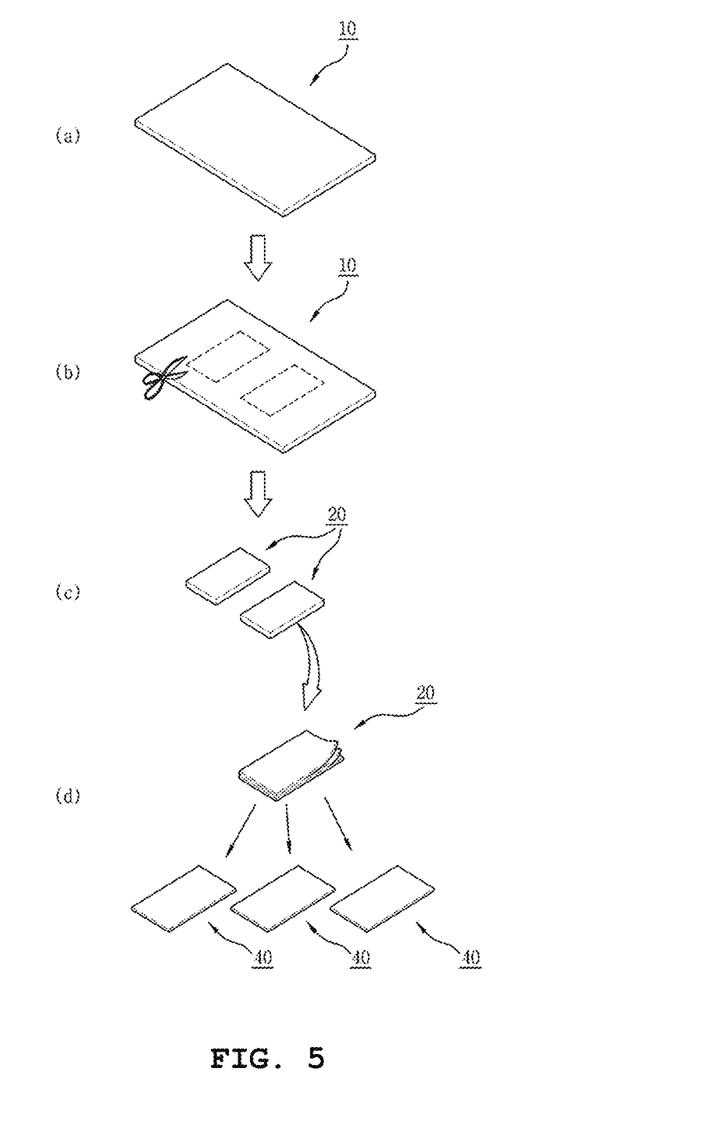
FIG. 5 illustrates the process of manufacturing the dental barrier membrane of Example 3 according to the present invention.

In a further modification, the method of manufacturing a dental barrier membrane using a silk matrix of Example 3 according to the present invention, as illustrated in FIG. 5, is specified below.

1. First Step: Preparation of Silk Matrix Pieces Having First Thickness

A silk matrix having a cross-section with a first thickness, produced from silkworms, is subjected to planar division into two or more pieces having an appropriate shape, thus forming silk matrix pieces 20 having the first thickness.

In this case, the silk matrix pieces 20 having the first thickness are formed in the same manner as in the first step of the description of FIG. 3.

When the first thickness of the silk matrix pieces 20 thus formed is suitable for use in a dental barrier membrane, such silk matrix pieces may be used without change. In the case where these silk matrix pieces are thick and difficult to use, they should be additionally subjected to the following second step so as to have a thickness suitable for dental barrier membranes. The second step is described below.

2. Second Step: Preparation of Silk Matrix Pieces (Dental Barrier Membrane) Having Second Thickness Silk matrix pieces 40 having a second thickness, suitable for use as a dental barrier membrane, are prepared.

The silk matrix pieces 20 having the first thickness, obtained in the first step, are configured as illustrated in FIG. 2B such that yarns resulting from spinning cocoons from the silkworms are stacked in a height direction to thus form various thicknesses (multiple layers).

The first thickness of the silk matrix pieces 20 may vary depending on the number of silkworms used to prepare the silk matrix and the period of time that the silkworms require to spin cocoons.

When the silk matrix pieces 20 having the first thickness are suitable for use in a dental barrier membrane, they may be used without change. As illustrated in FIG. 5, in the case where the silk matrix pieces are thick, each of the silk matrix pieces having the first thickness, obtained in the first step, is subjected to thickness division into two or more pieces having an appropriate thickness so as to serve as a dental barrier membrane, yielding silk matrix pieces 40 having a second thickness. As such, the second thickness is less than the first thickness owing to the thickness division.

The silk matrix pieces 40 having a second thickness may be used unchanged as a dental barrier membrane for any purpose. Further, packing or sterile treatment and chemical treatment may be additionally performed, as necessary.

A better understanding of the present invention may be obtained through the following examples and test examples, which are set forth to illustrate, but are not to be construed to limit the scope of the present invention.

<Example 1> Manufacture of Dental Barrier Membrane 1 of the Invention

As illustrated in FIG. 1, 15 mature silkworms were placed on a sheet, and the sheet was gradually tilted at 20° with respect to the ground. After 1 hr, the sheet was gradually tilted again in the opposite direction. In this way, the silkworms spun cocoons while moving, yielding a silk matrix 10 in the conformation shown in FIG. 2A.

The above tilting process was performed for one day, equilibrium was maintained for two days, and the above tilting process was performed again, whereby a silk matrix was produced from the silkworms in about three days. The silk matrix had a thickness of about 0.01 mm.

As shown in FIG. 3, the silk matrix 10 was cut using scissors so as to undergo planar division in a rectangular shape, thus forming silk matrix pieces 20, which were then sterilized, thereby manufacturing a dental barrier membrane 1 according to the present invention.

<Example 2> Manufacture of Dental Barrier Membrane 2 of the Invention

As illustrated in FIG. 1, 30 mature silkworms were placed on a sheet, and the sheet was gradually tilted at 20° with respect to the ground. After 1 hr, the sheet was gradually tilted again in the opposite direction. In this way, the silkworms spun cocoons while moving, yielding a silk matrix 10 in the conformation shown in FIG. 2B.

The above tilting process was performed for one day, equilibrium was maintained for two days, and the above tilting process was performed again, whereby a silk matrix was produced from the silkworms in about three days. The silk matrix had a thickness of about 0.7 mm.

As shown in FIG. 4, the silk matrix 10 having a thickness of 0.7 mm was peeled so as to undergo thickness division, thus forming silk matrix portions 30 having a thickness of 0.4 mm, which were then sterilized, thereby manufacturing a dental barrier membrane 2 according to the present invention.

<Example 3> Manufacture of Dental Barrier Membrane 3 of the Invention

As illustrated in FIG. 1, 30 mature silkworms were placed on a sheet, and the sheet was gradually tilted at 20° with respect to the ground. After 1 hr, the sheet was gradually tilted again in the opposite direction. In this way, the silkworms spun cocoons while moving, yielding a silk matrix 10 in the conformation shown in FIG. 2B.

The above tilting process was performed for one day, equilibrium was maintained for two days, and the above tilting process was performed again, whereby a silk matrix was produced from the silkworms in about three days. The silk matrix had a thickness of about 0.7 mm.

The silk matrix was then cut using scissors so as to undergo planar division in a rectangular shape, thus forming silk matrix pieces 20.

As illustrated in FIG. 5, the silk matrix pieces 20 having a thickness of 0.7 mm were peeled so as to undergo thickness division, thus obtaining silk matrix pieces 40 having a thickness of 0.4 mm, which were then sterilized, yielding a dental barrier membrane 3 according to the present invention.

\<Test Example 1\> Evaluation of Morphology of Dental Barrier Membrane of the Invention 1. Test Method In order to evaluate the morphology of the silk matrix of FIGS. 2A and 2B, it was observed at a predetermined magnification using SEM, and commercially available membranes, namely a collagen barrier membrane and a PTFE (polytetrafluoroethylene) membrane, were used as controls.

2. Test Results

Figure 6:
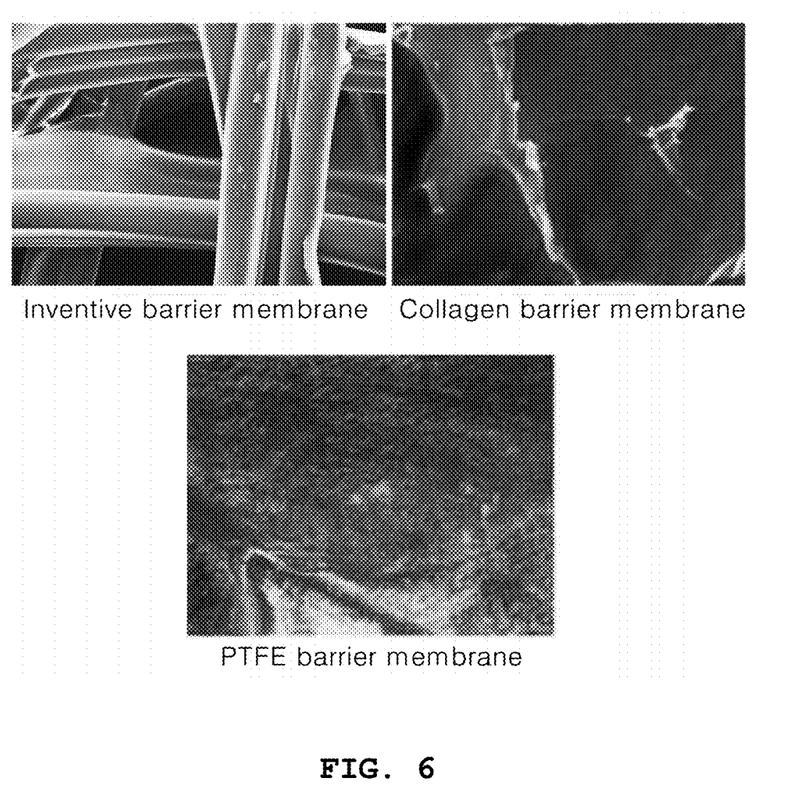
FIG. 6 illustrates the scanning electron microscopy (SEM) images of the morphologies of the dental barrier membrane according to the present invention and the membranes used as controls.

As illustrated in FIG. 6, when the morphologies of the membrane of the invention and the control membranes were observed using SEM, there was a morphological difference in terms of the pore shape or the membrane surface. The collagen barrier membrane was configured such that relatively large pores were uniformly arranged on the surface of the planar membrane, and the PTFE barrier membrane was configured such that pores having a predetermined size and interval therebetween were formed on the surface of the planar membrane.

On the other hand, the surface of the dental barrier membrane according to the present invention was configured such that fiber strands having various thicknesses were repeatedly irregularly stacked, and many pores were observed between the stacked fiber strands. Thus, the dental barrier membrane according to the present invention has a porous structure having high nutrient and water permeability and is thus expected to be effective at bone regeneration by facilitating the supply of nutrients and water necessary for the formation of new bone when transplanted into the bone defect.

\<Test Example 2\> Measurement of Mechanical Properties of Dental Barrier Membrane of the Invention 1. Test Method In order to measure the mechanical properties of the dental barrier membrane of Example 3 according to the present invention, the dental barrier membrane was subjected to tensile testing together with a commercially available collagen barrier membrane and a commercially available PTFE barrier membrane as controls, using a universal testing machine (DAEYEONG, Korea).

Analytical samples were manufactured to a size of 5×20 (width×length) mm, and the manufactured membrane was stretched at a gauge length of 10 mm and a rate of 10 mm/min.

Since the intraoral environment is wet due to the continuous secretion of saliva, the samples were measured for mechanical properties (tensile strength) in a wet state, achieved through immersion in saline for 1 hr.

2. Test Results

TABLE 1

| Membrane type | Tensile strength (MPa) | Elastic modulus |
|---|---|---|
| Inventive dental barrier membrane | 26.4 ± 1.6 | 35.7 ± 3.6 |
| Collagen barrier membrane | 3.5 ± 1.3 | 9.6 ± 2.2 |
| PTFE barrier membrane | 4.3 ± 1.7 | 304.5 ± 5.3 |

Table 1 shows the results of measurement of tensile strength and elastic modulus of the dental barrier membrane according to the present invention in a wet state, along with those of the control membranes. The tensile strength was measured to be 26.4±1.6 MPa in the dental barrier membrane according to the present invention, 3.5±1.3 MPa in the collagen barrier membrane, and 4.3±1.7 MPa in the PTFE barrier membrane. Also, the elastic modulus was measured to be 35.7±3.6 in the dental barrier membrane according to the present invention, 9.6±2.2 in the collagen barrier membrane, and 304.5±5.3 in the PTFE barrier membrane.

Based on the above results, the dental barrier membrane according to the present invention exhibited tensile strength about 9 times as high as that of the collagen barrier membrane, and about times as high as that of the PTFE barrier membrane, thereby resulting in superior tensile strength in comparison with existing membranes. Also, the dental barrier membrane according to the present invention showed an elastic modulus about 4 times as high as that of the collagen barrier membrane, and thus its elasticity was improved compared to existing collagen barrier membranes.

In conclusion, since a membrane, which is transplanted in vivo for tissue regeneration and bone regeneration, has to possess tensile strength and elasticity so as to satisfactorily withstand pressure in the bone defect while uniformly retaining its morphology, the dental barrier membrane according to the present invention can be confirmed to be appropriate for use as a dental barrier membrane owing to its tensile strength and elasticity, which are superior to those of commercially available control membranes.

\<Test Example 3\> Evaluation of Bone Regenerative Capacity of Dental Barrier Membrane of the Invention 1. Test Method The dental barrier membrane of Example 3 according to the present invention and the collagen barrier membrane and the PTFE barrier membrane as controls were transplanted into rabbit bone defects.

In order to check the formation of new bone after transplantation of the membrane, the dental barrier membrane of the invention was subjected to staining with Hematoxylin Eosin and histological analysis, 4 weeks and 8 weeks after surgery. As the controls, the collagen barrier membrane and the PTFE barrier membrane were subjected to Masson's trichrome staining and histological analysis.

2. Test Results

Figure 7:
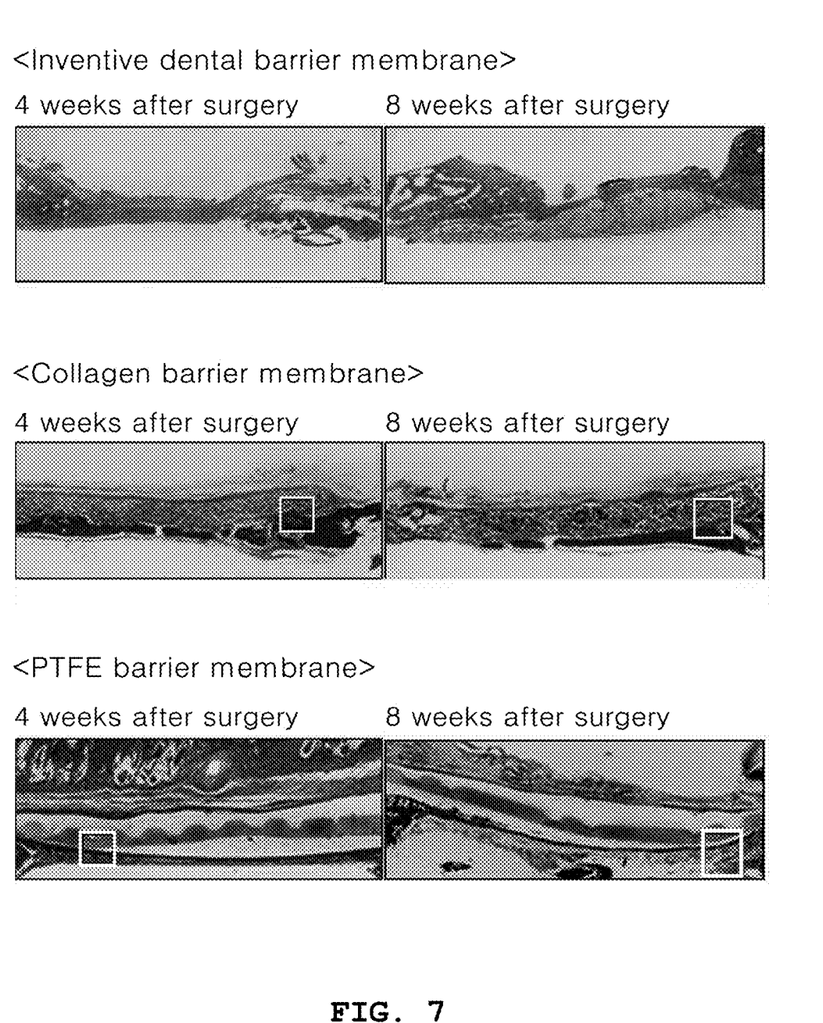
FIG. 7 illustrates the results of staining of the new bones formed after the dental barrier membrane according to the present invention and the membranes used as the controls were transplanted into the bone defects.

The cross-sections of the tissues were observed, and the results are shown in FIG. 7. Specifically, FIG. 7 illustrates the cross-sections of the tissues, 4 weeks and 8 weeks after transplantation of respective membranes. Based on the results of observations of tissue cross-sections on the fourth week, the cross-section of the tissue into which the dental barrier membrane of the invention was transplanted showed that the dark grey portion deeply penetrated into the tissue and was uniformly distributed. This means that new bone was actively formed in the bone defect into which the dental barrier membrane of the invention was transplanted.

In contrast, for the collagen barrier membrane, the grey portion was partially distributed in the tissue, and for the PTFE barrier membrane, the grey portion was difficult to detect (mature bone: grey, immature bone: dark black).

Based on the results of tissue cross-sections on the eighth week, the tissue into which the membrane of the invention was transplanted was changed, the grey portion detected on the fourth week turning to dark grey while forming new bone.

In the case of the collagen barrier membrane, the formation of new bone, marked by the grey, was seen in the tissue cross-section, but the dark black portion remained around the new bone, based on which the formation of new bone was determined to still be progressing. In the case of the PTFE barrier membrane, the grey portion was seen in the tissue, based on which the formation of new bone was determined to have begun.

The proportion of the formed new bone was determined through histological analysis. The results are graphed in FIG. 8. Here, the membrane used and the proportion of formed new bone are shown on the X-axis and the Y-axis, respectively.

Figure 8:
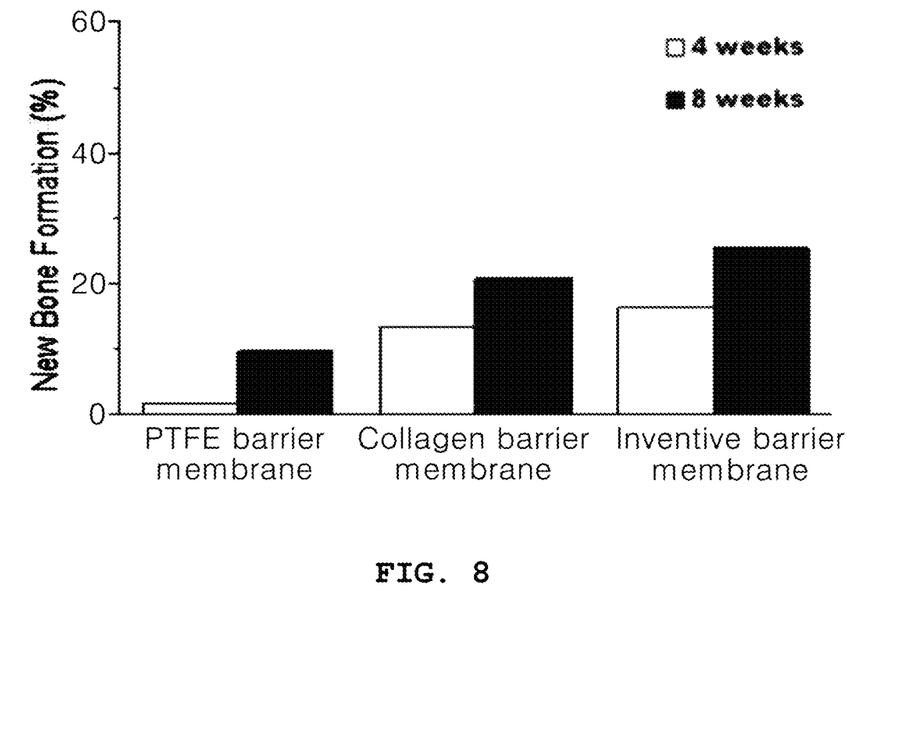
FIG. 8 is a graph illustrating the proportion of new bones formed after the dental barrier membrane according to the present invention and the membranes used as the controls were transplanted into the bone defects.

When the dental barrier membrane of the invention was transplanted into the bone defect, the proportion of new bone was 18% on the fourth week and 25% on the eighth week. For the collagen barrier membrane used as the control, the proportion of new bone was 15% on the fourth week and 20% on the eighth week. Also, the PTFE barrier membrane manifested a proportion of new bone of 1% on the fourth week and 10% on the eighth week. The formation of new bone by the dental barrier membrane of the invention was increased a maximum of about four times compared to when using the controls.

Therefore, the dental barrier membrane of the invention can exhibit superior bone regenerative capacity when applied to bone defects, and is thus suitable for use as a dental barrier membrane.

Although the preferred examples and test examples of the present invention have been disclosed for illustrative purposes, those skilled in the art will appreciate that various modifications, additions and substitutions are possible, without departing from the scope and spirit of the invention as disclosed in the accompanying claims. The scope of the present invention is shown not in the above description but in the claims, and all differences within the range equivalent thereto will be understood to be incorporated in the present invention.

What is claimed is:

1. A method of manufacturing a dental harder membrane using a silk matrix, comprising: placing silkworms on a sheet; inducing the silkworms to spin cocoons on the sheet by moving the sheet and forming the silk matrix by preventing the silkworms from falling off the sheet and forming a pupal casing with the cocoons, the silk matrix having a cross-section with a first thickness;
   wherein the sheet is moved in a manner of being rotated, repeatedly tilted upward and downward, or vibrated; and subjecting the silk matrix to planar division into two or more silk matrix pieces having a predetermined shape with the first thickness.

2. A method of manufacturing a dental barrier membrane using a silk matrix, comprising: placing silkworms on a sheet; inducing the silkworms to spin cocoons on the sheet by moving the sheet and forming the silk matrix by preventing the silkworms from falling off the sheet and forming a pupal casing with the cocoons, the silk matrix having a cross-section with a first thickness;
   wherein the sheet is moved in a manner of being rotated, repeatedly tilted upward and downward, or vibrated; and subjecting the silk matrix to thickness division into two or more silk matrix portions having a second thickness, which is less than the first thickness.

3. A method of manufacturing a dental barrier membrane using a silk matrix, comprising: placing silkworms on a sheet; inducing the silkworms to spin cocoons on the sheet by moving the sheet and forming the silk matrix by preventing the silkworms from falling off the sheet and forming a pupal casing with the cocoons, the silk matrix having a cross-section with a first thickness;
   wherein the sheet is moved in a manner of being rotated, repeatedly tilted upward and downward, or vibrated; subjecting the silk matrix to planar division into two or more silk matrix pieces having a predetermined shape with the first thickness; and subjecting each of the silk matrix pieces having the first thickness to thickness division into two or more silk matrix pieces having a second thickness, which is less than the first thickness.

4. The method of claim 1, further comprising stacking the silk matrix pieces having the first thickness obtained in the first step.

5. The method of claim 2, further comprising stacking the silk matrix portions having the second thickness obtained in the first step.

6. The method of claim 3, further comprising stacking the silk matrix pieces having the second thickness obtained in the second step.

7. The method claim 1, further comprising performing at least one sterilization process, before or after each step.

8. The method claim 2, further comprising performing at least one sterilization process, before or after each step.

9. The method claim 3, further comprising performing at least one sterilization process, before or after each step.

10. The method claim 4, further comprising performing at least one sterilization process, before or after each step.

11. The method claim 5, further comprising performing at least one sterilization process, before or after each step.

12. The method claim 6, further comprising performing at least one sterilization process, before or after each step.

13. A method of manufacturing a dental barrier membrane for promoting a new bone tissue in bone defects using a silk matrix, comprising: placing silkworms on a sheet; inducing the silkworms to spin cocoons on the sheet by moving the sheet and forming the silk matrix by preventing the silkworms from falling off the sheet and forming a pupal casing with the cocoons, the silk matrix having a cross-section with a first thickness; wherein the sheet is moved in a manner of being rotated, repeatedly tilted upward and downward, or vibrated; subjecting the silk matrix to planar division into two or more silk matrix pieces having a predetermined shape with the first thickness; and implanting one of the two or more silk matrix pieces onto the bone defects of a subject, wherein the new bone tissue is formed in the bone defects.

14. A method of manufacturing a dental barrier membrane for promoting a new bone tissue in bone defects using a silk matrix, comprising: placing silkworms on a sheet; inducing the silkworms to spin cocoons on the sheet by moving the sheet and forming the silk matrix by preventing the silkworms from falling off the sheet and forming a pupal casing with the cocoons, the silk matrix having a cross-section with a first thickness; wherein the sheet is moved in a manner of being rotated, repeatedly tilted upward and downward, or vibrated; subjecting the silk matrix to thickness division into two or more silk matrix portions having a second thickness, which is less than the first thickness; and implanting one of the two or more silk matrix portions onto the bone defects of a subject, wherein the new bone tissue is formed in the bone defects.

15. A method of manufacturing a dental barrier membrane for promoting a new bone tissue in bone defects using a silk matrix, comprising: placing silkworms on a sheet; inducing the silkworms to spin cocoons on the sheet by moving the sheet and forming the silk matrix by preventing the silkworms from falling off the sheet and forming a pupal casing with the cocoons, the silk matrix having a cross-section with a first thickness; wherein the sheet is moved in a manner of being rotated, repeatedly tilted upward and downward, or vibrated; subjecting the silk matrix to planar division into two or more silk matrix pieces having a predetermined shape with the first thickness;

subjecting each of the silk matrix pieces having the first thickness to thickness division into two or more silk matrix pieces having a second thickness, which is less than the first thickness; and implanting one of the two or more silk matrix pieces and/or the two or more matrix portions onto the bone defects of a subject, wherein the new bone tissue is formed in the bone defects.

16. The method claim 13, further comprising performing at least one sterilization process, before or after each step.

17. The method claim 14, further comprising performing at least one sterilization process, before or after each step.

18. The method claim 15, further comprising performing at least one sterilization process, before or after each step.

* * * * *